(12) United States Patent
Hsieh

(10) Patent No.: US 6,385,278 B1
(45) Date of Patent: May 7, 2002

(54) METHOD AND APPARATUS FOR REGION OF INTEREST MULTISLICE CT SCAN

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/560,171

(22) Filed: Apr. 28, 2000

(51) Int. Cl.$^7$ ................................................. A61B 6/03
(52) U.S. Cl. ................................ 378/8; 378/15; 378/20
(58) Field of Search ........................... 378/4, 8, 15, 16, 378/20, 901

(56) References Cited

U.S. PATENT DOCUMENTS

| | | | |
|---|---|---|---|
| 4,118,631 A | * 10/1978 | Froggatt | .................... 378/65 |
| 5,485,492 A | 1/1996 | Pelc | |
| 5,610,963 A | 3/1997 | Hsieh | |
| 5,644,614 A | 7/1997 | Toth et al. | |
| 5,864,598 A | 1/1999 | Hsieh et al. | |
| 6,023,494 A | 2/2000 | Senzig et al. | |
| 6,041,097 A | 3/2000 | Roos et al. | |
| 6,246,742 B1 | * 6/2001 | Besson et al. | .................... 378/8 |
| 6,272,201 B1 | 8/2001 | Pan | |

* cited by examiner

Primary Examiner—David V. Bruce
(74) Attorney, Agent, or Firm—Carl B. Horton, Esq.; Armstrong Teasdale LLP

(57) ABSTRACT

In one embodiment, the present invention is a method for reducing radiation dosage when scanning an region of interest of an object with a multi-slice computed tomography (CT) imaging system. The method includes steps of collimating the radiation beam of the CT imaging system into a fan-shaped radiation beam having at least a first region and a second region, the first region having a lesser angular extent than that of the second region; scanning an object having a region of interest (ROI) with the collimated radiation beam- and reconstructing an image of the object using the attenuation measurements collected during the scan, wherein the reconstruction utilizes attenuation measurements collected using the second region of the radiation beam to estimate projection data from portions of the object outside of the ROI blocked by the collimation.

35 Claims, 3 Drawing Sheets

METHOD AND APPARATUS FOR REGION OF INTEREST MULTISLICE CT SCAN

BACKGROUND OF THE INVENTION

This invention relates generally to methods and apparatus for CT imaging, and more particularly to methods and apparatus for reducing an x-ray dose to a patient during a computed tomography (CT) imaging scan.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In recent years, radiologists have become increasingly concerned about reducing the x-ray dose to a patient during a CT examination. In Europe, for example, strict guidelines have been instituted to prevent potential danger of exposing patients and operators to excessive x-ray radiation. New uses of CT imaging have increased the interest in limiting x-ray exposure of patients. In cardiac screening CT, for example, asymptomatic patients undergo routine CT scans to detect calcification in coronary arteries. In this and in other types of screening examinations, x-ray dose to the patient should be kept to a minimum.

It would therefore be desirable to provide methods and apparatus for reducing an amount of x-ray dosage a patient receives during a CT imaging scan. More particularly, it would be desirable to minimize x-ray dosage to regions outside an organ of interest (OOI) whenever a relatively small organ, such as a heart, is the OOI being scanned.

BRIEF SUMMARY OF THE INVENTION

There is therefore provided, in one embodiment, a method for scanning an region of interest of an object with a multi-slice computed tomography (CT) imaging system that reduces a radiation dose received by the object during a scan. The method includes steps of collimating the radiation beam of the CT imaging system into a fan-shaped radiation beam having at least a first region and a second region, the first region having a lesser angular extent than that of the second region, scanning an object having a region of interest (ROI) with the collimated radiation beam; and reconstructing an image of the object using the attenuation measurements collected during the scan, wherein the reconstruction utilizes attenuation measurements collected using the second region of the radiation beam to estimate projection data from portions of the object outside of the ROI blocked by the collimation.

The above described embodiment reduces an amount of x-ray dosage a patient receives during a CT imaging scan. X-ray dosage outside of an organ of interest (OOI) is minimized whenever a relatively small organ, such as a heart, is the OOI being scanned.

DETAILED DESCRIPTION OF THE INVENTION

Figure 1:
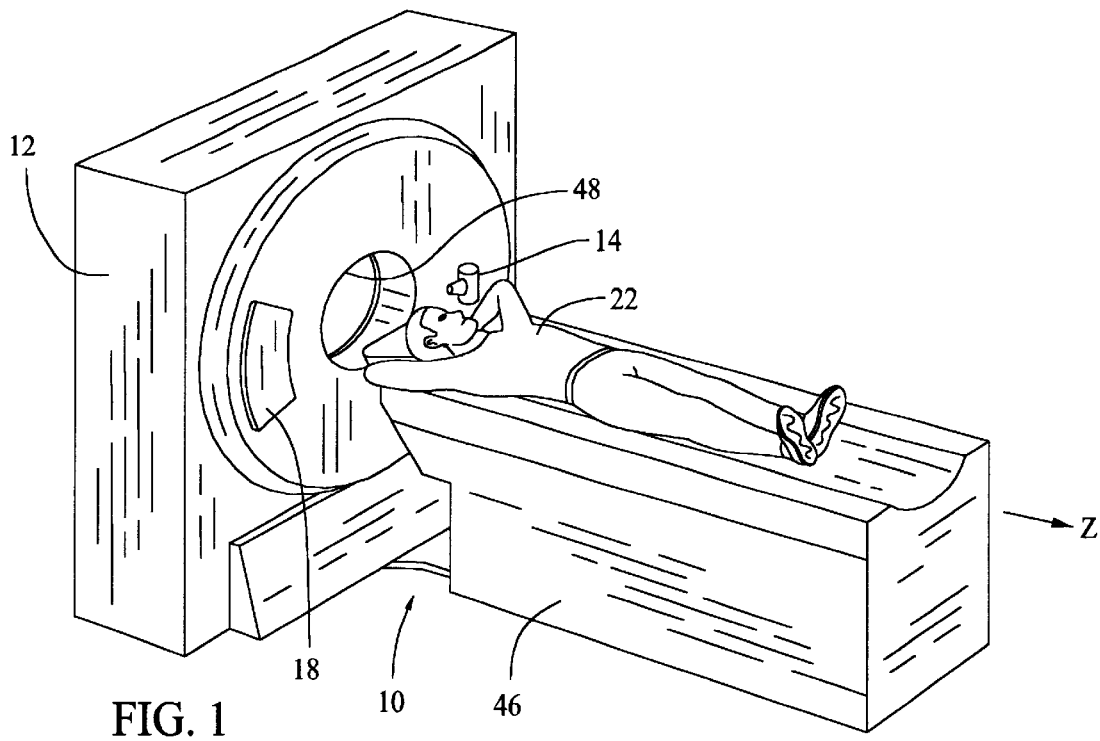
FIG. 1 is a pictorial view of a CT imaging system.
Figure 2:
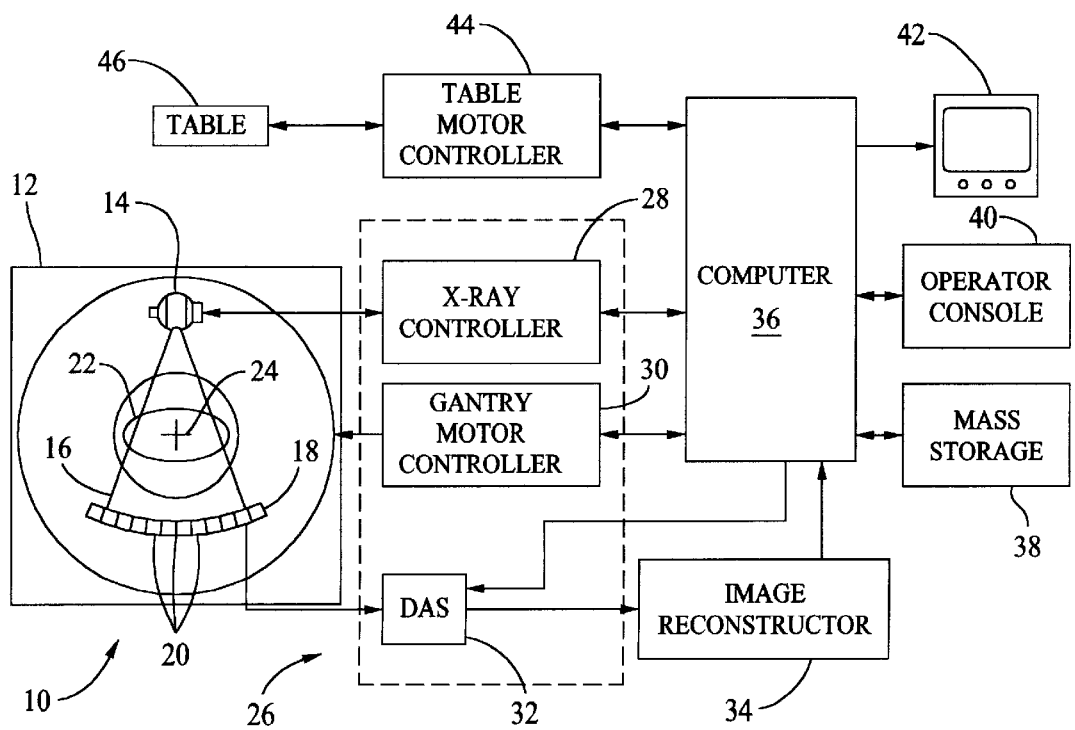
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

For some types of examinations, interest is directed mainly to a region of interest (ROI) of within an object 22. When object 22 is a patient and ROI is a relatively small organ of interest (OOI), it is particularly desirable to minimize patient dose outside the OOI. Because projection readings outside the OOI are useful mainly for tomographic reconstruction, it has been found that these readings need not be highly accurate in order to produce excellent images inside the OOI using a fast magnitude decay reconstruction filter kernel. Projections of a multi-slice scanner do not change quickly from row to row because human anatomy does not change much over several millimeters along a patient's axis. Therefore, in one embodiment, projection information collected on one of the rows is used to estimate projection values on other rows outside the OOI. The patient is irradiated fully for all rows for the region inside the OOI. For the region inside the OOI, only a small portion of the entire detector is exposed to x-rays.

Figure 3:
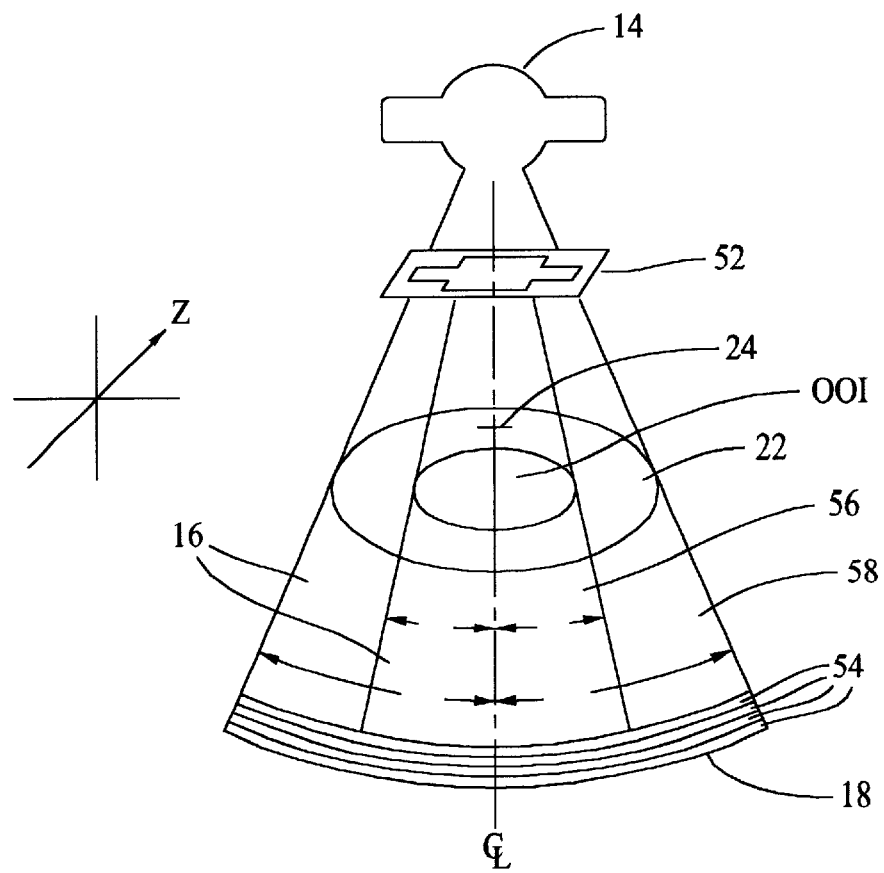
FIG. 3 is a simplified pictorial view of the x-ray source, x-ray beam, and detector of FIGS. 1 and 2, showing a multi-slice detector and a pre-patient x-ray collimator.

In one exemplary embodiment and referring to FIG. 3, a region of radiation beam 16 that irradiates patient 22 outside OOI is limited by a pre-patient collimator 52. Collimator 52 in this embodiment is a shield that is supported in a fixed position relative to x-ray source 14 so that x-ray source 14 and collimator 52 rotate together on gantry 12. However, in another embodiment, an adjustable collimator 52 is employed. In yet another embodiment, collimator 52 is physically removable from the path of radiation beam 16.

Collimator 52 is configured so that a first, relatively thick collimated region 56 of radiation beam 16 encompasses OOI. ("Thick" as used herein, refers to a z-axis dimension.) Collimator 52 is also configured, in one embodiment, to produce a second, less thick region 58 of radiation beam 16 having a thickness exposing only one row of a plurality of rows 54 of detector 18. Expressed in another way, fan-shaped first region 56 has a lesser angular extent $2\gamma_0$ than does fan-shaped second region 58, which has angular extent $2\gamma$. (The factor 2 is introduced here to simplify certain equations below.)

Figure 4:
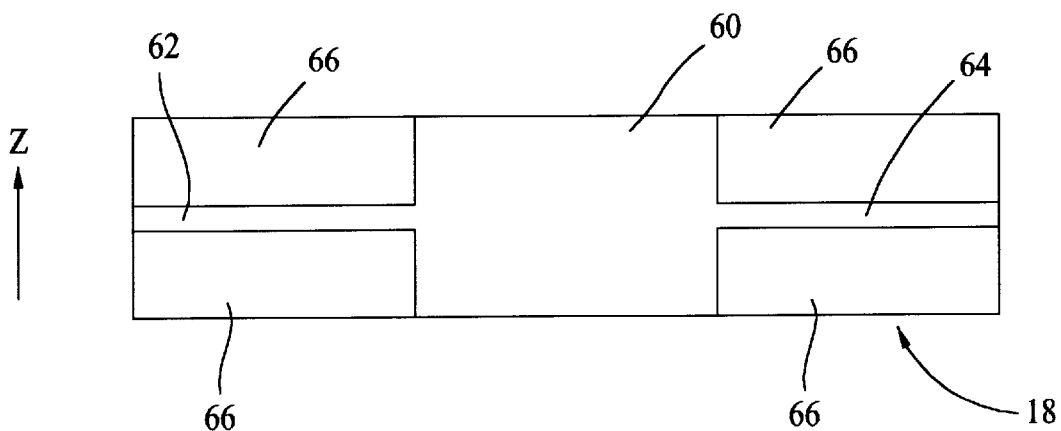
FIG. 4 is a drawing illustrating partial irradiation of the detector using the collimated x-ray beam of FIG. 3.

The effect of the collimation of radiation beam 16 on detector 18 during a scan may be better understood by reference to FIG. 4. (The curvature of detector 18 is not shown in FIG. 4.) First region 56 of radiation beam 16 impinges OOI of patient 22 and detector elements 20 in region 60 of detector 18. (Individual detector elements 20 are not shown in FIG. 4.) Second region 58 impinges a wider portion of patient 22 outside of OOI. Attenuation measurements from this wider region include measurements from detector elements 20 in wing-shaped regions 62 and 64 of detector 18. Regions 66 receive little, if any, radiation from radiation beam 16. However, in one embodiment, at least some detector elements 20 in regions 66 receive radiation having reduced intensity from a penumbra of radiation beam 16. For simplicity, the present discussion and the claims below conform to a convention that ignores the penumbra in measuring collimator "limits" of a radiation beam. Therefore, a penumbra of radiation beam 16 is considered to be outside the collimator-limited edge of the beam.

In one exemplary embodiment, detector 18 is an eight-slice detector having eight rows 54 (not shown in FIG. 4). Regions 62 and 64 are each one detector row 54 thick in the z-direction. In another exemplary embodiment, regions 62 and 64 are less than one detector row 54 thick in the z-direction. Other embodiments have collimated radiation beams that produce regions 60, 62, and 64 having thicknesses and/or shapes different from those shown and described. However, in each embodiment, radiation beam 16 is collimated into a fan-shaped beam having at least two regions 56 and 58, with the first region having a lesser angular extent than the second, resulting in only a portion of object 22 outside of ROI receiving a radiation dose.

Considering one exemplary embodiment in detail, let $P(\gamma, k)$ denote projection data detected by detector 18 during a scan with detector angle $\gamma$ and detector row k. Only the nth detector row of detector rows 54 is fully exposed to x-rays for the entire projection. Denoting a detector angle that corresponds to a boundary of the OOI by $\gamma_0$, the entire OOI region is denoted by $(-\gamma_0, \gamma_0)$ An angular extent of region 56 is limited to substantially an angle subtended by the OOI, and region 58 has an angular extent at least equal to that of detector 18.

Object 22 is scanned with imaging system 10, and attenuation data is collected by detector 18. Projection data for detector row k (k#n) is determined by an equation written:

$$P(\gamma, k) = \begin{cases} P(\gamma, k) & -\gamma_0 + \delta \leq \gamma \leq \gamma_0 - \delta \\ \theta(\gamma)P(\gamma, k) + [1 - \theta(\gamma)]P(\gamma, n) & \text{otherwise} \end{cases}$$

where:

$$\theta(\gamma) = 3w^2(\gamma) - 2w^3(\gamma),$$

$$w(\gamma) = \begin{cases} \dfrac{\gamma + \gamma_0}{\delta} & -\gamma_0 \leq \gamma < -\gamma_0 + \delta \\ 1 & -\gamma_0 + \delta \leq \gamma < \gamma_0 - \delta \\ \dfrac{\gamma_0 - \gamma}{\delta} & \gamma_0 - \delta \leq \gamma < \gamma_0 \\ 0 & \text{otherwise,} \end{cases}$$

and $\delta$ is a parameter that defines a width of a transition region.

This equation uses projection data for one row n to replace projection data for other rows outside of the OOI. The "feathering" or "blending" that takes place mainly removes discontinuities encountered during projection substitution. In other embodiments, other techniques are used to blend the two signals together.

Based on the above equation, projections outside the OOI for detector rows other than n are given a weighting function of zero. Therefore, these projection samples are not contributing to the final reconstructed images. In one embodiment, these projection samples are omitted from data collection.

Attenuation measurements from a penumbra of radiation beam 16 F provide some information that can be used for imaging an object 22. It is desirable to make use of all of the information collected. Therefore, in one embodiment, data from all detector rows are summed (after a logarithm operation) and the sum is used as a basis for projection estimation outside the OOI.

The techniques and apparatus of the present invention realize significant patient x-ray dose reduction. For example, in a cardiac study, a majority of a patient's heart can easily be fitted inside a 25 cm field of view (FOV). For a 50 cm FOV scanner, a scan of the patient's heart utilizes about 58% of the detector cells. For an eight-slice scanner, if only one detector row outside the OOI is selected for exposure (in fact, only exposure of a fraction of a detector row is needed), the additional exposed x-ray region is only 5% of an entire detector channel. Therefore, the overall dose saving is roughly 1.00−0.58−0.05=0.37, or 37% in an embodiment in which region 59 has an angular extent essentially coextensive with the 25 cm FOV.

To verify methods and apparatus of the present invention, a shoulder phantom was scanned in a helical scan mode having a 3:1 pitch. A shoulder phantom was selected as being representative of a "worst case" condition, because the densest bones are outside a center region for which reconstruction was to be attempted. For this experiment, δ was to be 20 channels wide. Projections for all rows (except one row adjacent a center of the detector) were truncated outside a 30 cm FOV. Equation 1 was then applied to produce all projections. An image was then reconstructed. Two other images were produced for comparison, one utilizing the entire FOV for the CT imaging system (54.7° for this system) and one utilizing the 30 cm FOV, but without truncation. Visually, no image difference was observed between the truncated image to which equation 1 was applied and the other two images. A difference image of the 30 cm FOV was produced from an image utilizing the entire FOV of the imaging system and the truncated image. This difference image showed no visible structures.

In embodiments described above, first beam region 56 was collimated so that fully-scanned region 60 was symmetrical with respect to an isocenter 24, i.e., the region selected was $-\gamma_0 < \gamma < \gamma_0$. In another embodiment, first beam region 56 is collimated asymmetrically, so that fully scanned region 60 is asymmetric. For example, the first beam is collimated as $-\gamma_1 < \gamma < \gamma_0$, where $\gamma_1 \neq \gamma_0$. An advantage of this approach is that it minimizes the impact of a transition region, because the two boundaries are not aligned.

Figure 5:
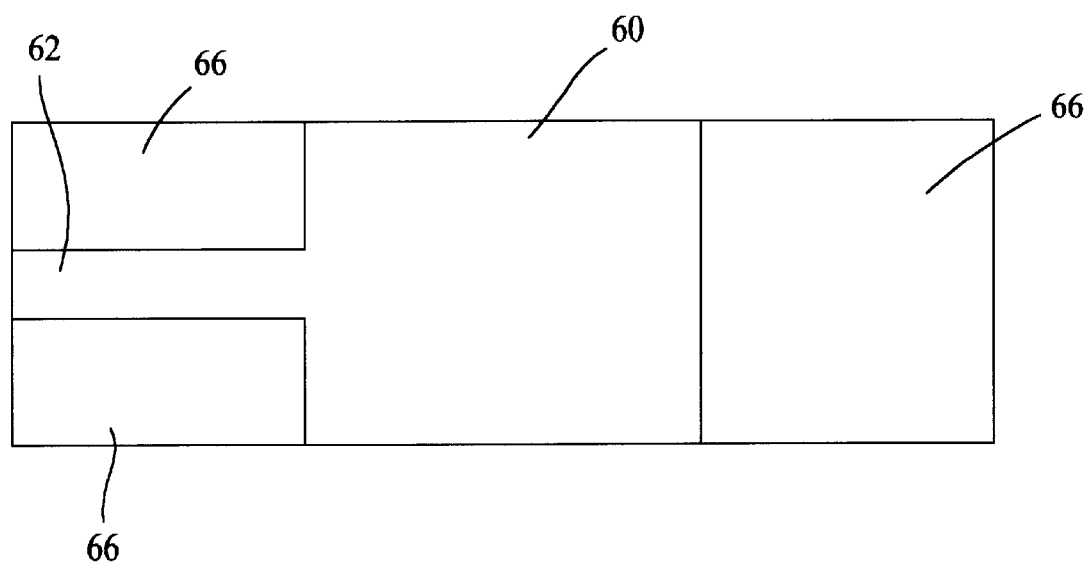
FIG. 5 is a drawing illustrating partial irradiation of the detector using a collimated x-ray beam having only one side wing.

In another embodiment, second region 58 is collimated to have only one side wing 62 or 64, but not both, as shown in FIG. 5. With scans of at least 360°, projection data from one side wing, e.g., side wing 62, is used in image reconstruction to fill in information from the missing side wing, e.g., side wing 64.

In yet another embodiment, the present invention is applied to a single-slice scanner in which a thicker region of an ROI is scanned than regions outside the ROI. In one embodiment and referring again to FIGS. 3 and 4, detector 18 has only one detector row in the z-axis direction. Beam 16 is collimated to have a thicker, first region 56 and a thinner, second region 58. During a scan, ROI is scanned in thicker, first region 56. In another embodiment, a plurality of scans are performed to acquire projection data for reconstructing a plurality of images of image of ROI, with table 46 indexed between scans. However, some of the plurality of scans are performed with a radiation beam collimated to have a reduced angular extent. The reduced angular extent is, for example, coextensive with ROI. Data acquired during one or more scans using a full angle of the radiation beam are used to supply missing information in the scans performed using a reduced angular extent of the radiation beam.

From the preceding description of various embodiments of the present invention, it is evident that a reduction in patient radiation dose is achieved in scanning an OOI, with little sacrifice in image quality. Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given radiation beam. Moreover, the system described herein performs an axial scan, however, the invention may be used with systems performing helical scans. Accordingly, the spirit and scope of the invention are to be limited only by the terms of the appended claims and legal equivalents.

While the invention has been described in terms of various specific embodiments, those skilled in the art will recognize that the invention can be practiced with modification within the spirit and scope of the claims.

What is claimed is:

1. A method for reducing radiation dosage during a region of interest scan (ROIS) of a multi-slice computed tomography (CT) imaging system having a radiation source generating a radiation beam and a multi-slice detector having a plurality of rows, the detector being configured to collect attenuation measurements of the radiation beam passing through an object to be imaged during a scan of the object, said method comprising the steps of:

collimating the radiation beam into a fan-shaped radiation beam having at least a first region and a second region, the first region having a lesser angular extent than that of the second region;

scanning an object having a region of interest (ROI) with the collimated radiation beam; and reconstructing an image of the object using the attenuation measurements collected during the scan, wherein said reconstruction utilizes attenuation measurements collected using the second region of the radiation beam to estimate projection data from portions of the object outside of the ROI blocked by said collimation.

2. A method in accordance with claim 1 wherein the object is a patient, and the ROI is an organ of interest (OOI) of the patient.

3. A method in accordance with claim 2 wherein said collimation is performed using a pre-patient collimator.

4. A method in accordance with claim 3 wherein collimating the radiation beam comprises limiting the angular extent of the first region to substantially an angle subtended by the OOI, and wherein said second region has an angular extent at least equal to that of the detector.

5. A method in accordance with claim 4 wherein scanning with the collimated beam comprises exposing only one row of detector cells to the second region of the collimated radiation beam.

6. A method in accordance with claim 5 wherein reconstructing an image of the object furthers comprises utilizing measurements collected from a portion of the detector in a penumbra of the collimated radiation beam.

7. A method in accordance with claim 5 further comprising the step of utilizing measurements collected from a portion of the detector collecting attenuation the ROI to remove discontinuities in the reconstructed images.

8. A method in accordance with claim 7 wherein detector row n is the row of detector cells exposed to radiation subtending a fall width of the detector, the OOI is bounded by a detector angle range $(-\gamma_0, \gamma_0)$, and the detector has a fall width of γ, and reconstructing an image of the object comprises determining projection data for rows k where k≠n, as:

$$P(\gamma, k) = \begin{cases} P(\gamma, k) & -\gamma_0 + \delta \le \gamma \le \gamma_0 - \delta \\ \theta(\gamma)P(\gamma, k) + [1 - \theta(\gamma)]P(\gamma, n) & \text{otherwise} \end{cases}$$

where:

$$\theta(\gamma) = 3w^2(\gamma) - 2w^3(\gamma)$$

and:

$$w(\gamma) = \begin{cases} \dfrac{\gamma + \gamma_0}{\delta} & -\gamma_0 \le \gamma < -\gamma_0 + \delta \\ 1 & -\gamma_0 + \delta \le \gamma < \gamma_0 - \delta \\ \dfrac{\gamma_0 - \gamma}{\delta} & \gamma_0 - \delta \le \gamma < \gamma_0 \\ 0 & \text{otherwise,} \end{cases}$$

where δ is a parameter that defines a width of a transition region for blending.

9. A method in accordance with claim 8 further comprising the step of collecting projection samples from the detector corresponding to regions of the patient outside the OOI only from one detector row n.

10. A method in accordance with claim 2 wherein the OOI is a heart, the CT imaging system has a 50 cm field of view (FOV), and the patient's heart fits inside a 25 cm FOV, and the first region of the radiation beam has an angular extent essentially coextensive with the 25 cm FOV.

11. A method in accordance with claim 10 wherein the detector is an eight slice detector having eight detector rows, and only one row n of the eight detector rows is exposed to the second region of the radiation beam.

12. A method in accordance with claim 11 wherein only a portion of row n is exposed to the second region of the radiation beam.

13. A method in accordance with claim 1 wherein collimating the radiation beam comprises collimating the first region of the radiation beam into a fan-shaped region that is symmetric with respect to an isocenter of the CT imaging system.

14. A method in accordance with claim 1 wherein collimating the radiation beam comprises collimating the first region of the radiation beam into a fan-shaped region that is asymmetric with respect to an isocenter of the CT imaging system.

15. A method in accordance with claim 1 wherein collimating the radiation beam comprises collimating the second region of the radiation beam so that the second region of the radiation beam has two wings relative to the first region of the radiation beam.

16. A method in accordance with claim 1 wherein:
collimating the radiation beam comprises the step of collimating the second region of the radiation beam so that the second region of the radiation beam has only one wing on a first side of the first region of the radiation beam;
scanning the object with the collimated radiation beam comprises the step of scanning the object over at least 360°; and
reconstructing an image of the object comprises using projection data obtained from the wing on the first side of the first region of the radiation beam to reconstruct portions of the image on both sides of the ROI.

17. A method for reducing radiation dosage during a region of interest scan (ROIS) of a computed tomography (CT) imaging system configured to acquire a single slice of projection data during a scan, the CT imaging system having a radiation source generating a radiation beam and a detector configured to collect attenuation measurements of the radiation beam passing through an object to be imaged during a scan of the object, said method comprising the steps of:
collimating the radiation beam so that the radiation beam has a thicker first region and a thinner second region;
scanning an object having a region of interest with the collimated radiation beam, so that a region of interest (ROI) of an object is scanned in the first region of the radiation beam; and
reconstructing an image of the object using the attenuation measurements collected during the scan.

18. A method for reducing radiation dosage during a region of interest scan (ROIS) of a computed tomography (CT) imaging system configured to acquire a single slice of projection data during a scan, the CT imaging system having a moveable table, a radiation source generating a radiation beam and a detector having detector configured to collect attenuation measurements of the radiation beam passing through an object to be imaged during a scan of the object, said method comprising the steps of:
scanning an object on the table a plurality of times, the object having a region of interest (ROI), some of the scans being performed while collimating the radiation beam to have a reduced angular extent and at least one scan being performed using a full angular extent of the radiation beam;
indexing the table between scans;
and reconstructing an image of the object, using data acquired during the at least one scan performed using a full extent of the radiation beam to supply missing information in the scans performed using a reduced angular extent of the radiation beam.

19. A multi-slice computed tomography (CT) imaging system for performing a region of interest scan (ROIS) using a reduced amount of radiation, said imaging system comprising:
a radiation source generating a radiation beam;
a collimator configured to collimate the radiation beam into a fan-shaped radiation beam having at least a first region and a second region, the first region having a lesser angular extent than that of the second region; and
a multi-slice detector having a plurality of rows, the detector being configured to collect attenuation measurements of the radiation beam passing through an object to be imaged during a scan of the object.

20. The imaging system of claim 19 configured to:
scan an object having a region of interest (ROI) with the collimated, fan-shaped radiation beam; and
reconstruct an image of the object using the attenuation measurements collected during the scan, wherein said reconstruction utilizes attenuation measurements collected using the second region of the radiation beam to estimate projection data from portions of the object outside of the ROI blocked by said collimator.

21. An imaging system in accordance with claim 20 wherein said pre-patient collimator is a pre-patient collimator.

22. An imaging system in accordance with claim 21 wherein said collimator is configured to collimate the radiation beam so that said second region has an angular extent at least equal to that of the detector.

23. An imaging system in accordance with claim 22 configured to expose only one row of detector cells to the second region of the collimated radiation beam.

24. An imaging system in accordance with claim 23 wherein to reconstruct an image of the object, said imaging system is configured to utilizing measurements collected from a portion of the detector in a penumbra of the collimated radiation beam.

25. An imaging system in accordance with claim 23 further configured to utilize measurements collected utilizing the first portion of the collimated radiation beam ROI to remove discontinuities in the reconstructed images.

26. An imaging system in accordance with claim 25 wherein detector row n is the one row of detector cells exposed to the second region of the collimated radiation beam, a ROI is bounded by a detector angle range $(-\gamma_0,\gamma_0)$, and the detector has a full width of $\gamma$, and said imaging system being configured to reconstruct an image of the object comprises said imaging system being configured to determine projection data for rows k where k≠n, as:

$$P(\gamma, k) = \begin{cases} P(\gamma, k) & -\gamma_0 + \delta \leq \gamma \leq \gamma_0 - \delta \\ \theta(\gamma)P(\gamma, k) + [1 - \theta(\gamma)]P(\gamma, n) & \text{otherwise} \end{cases}$$

where:

$\theta(\gamma)=3w^2(\gamma)-2w^3(\gamma)$ and:

$$w(\gamma) = \begin{cases} \dfrac{\gamma + \gamma_0}{\delta} & -\gamma_0 \leq \gamma < -\gamma_0 + \delta \\ 1 & -\gamma_0 + \delta \leq \gamma < \gamma_0 - \delta \\ \dfrac{\gamma_0 - \gamma}{\delta} & \gamma_0 - \delta \leq \gamma < \gamma_0 \\ 0 & \text{otherwise,} \end{cases}$$

where $\delta$ is a parameter that defines a width of a transition region for blending.

27. An imaging system method in accordance with claim 26 further configured to collect projection samples from the detector outside the angular extent of the first region of the collimated radiation beam only from one detector row n.

28. An imaging system in accordance with claim 20 wherein the first region of the radiation beam has an angular extent essentially coextensive with a 25 cm FOV of an object, and the second region of the radiation beam has an angular extent at least equal to that of the detector.

29. An imaging system in accordance with claim 28 wherein the detector is an eight slice detector having eight detector rows, and only one row n of the eight detector rows is exposed to the second region of the radiation beam.

30. An imaging system in accordance with claim 29 wherein only a portion of row n is exposed to the second region of the radiation beam.

31. An imaging system in accordance with claim 20 wherein said collimator is configured to collimate the first region of the radiation beam into a fan-shaped region that is symmetric with respect to an isocenter of the CT imaging system.

32. An imaging system in accordance with claim 20 wherein said collimator is configured to collimate the first region of the radiation beam into a fan-shaped region that is asymmetric with respect to an isocenter of the CT imaging system.

33. An imaging system in accordance with claim 20 wherein said collimator is configured to collimate the second region of the radiation beam so that the second region of the radiation beam has two wings relative to the first region of the radiation beam.

34. An imaging system in accordance with claim 20 wherein:

said collimator is configured to collimate the second region of the radiation beam so that the second region of the radiation beam has only one wing on a first side of the first region of the radiation beam; and said imaging system is configured to perform a scan of at least 360° and to reconstruct an image of the object comprises using projection data obtained from the wing on the first side of the first region of the radiation beam to reconstruct portions of the image on both sides of the ROI.

35. A computed tomography (CT) imaging system for reducing radiation dosage during a region of interest scan (ROIS), said imaging system being configured to acquire a single slice of projection data during a scan, said imaging system comprising a radiation source configured to generate a radiation beam and a detector configured to collect attenuation measurements of the radiation beam passing through an object to be imaged during a scan of the object, said imaging system also being configured to:

collimate the radiation beam so that the radiation beam has a thicker first region and a thinner second region;

scan an object having a region of interest with the collimated radiation beam, so that a region of interest (ROI) of an object is scanned in the first region of the radiation beam; and reconstruct an image of the object using the attenuation measurements collected during the scan.

* * * * *

UNITED STATES PATENT AND TRADEMARK OFFICE
CERTIFICATE OF CORRECTION

PATENT NO.     : 6,385,278 B1
DATED          : May 7, 2002
INVENTOR(S)    : Jiang Hsieh It is certified that error appears in the above-identified patent and that said Letters Patent is hereby corrected as shown below:

Column 6,
Line 53, delete "furthers" insert therefor -- further --.
Lines 62 and 63, delete "fall" insert therefor -- full --.

Signed and Sealed this

Twenty-first Day of October, 2003

JAMES E. ROGAN
*Director of the United States Patent and Trademark Office*